United States Patent
Tang

Patent Number: 5,395,968
Date of Patent: Mar. 7, 1995

[54] INTERMEDIATES AND PROCESS FOR PREPARING MAGENTA COUPLERS

[75] Inventor: Ping-Wah Tang, Rochester, N.Y.

[73] Assignee: Eastman Kodak Company, Rochester, N.Y.

[21] Appl. No.: 3,697

[22] Filed: Jan. 13, 1993

[51] Int. Cl.$^6$ .......................................... C07C 321/14
[52] U.S. Cl. .................................. 564/162; 564/182
[58] Field of Search ............................. 564/162, 182

[56] References Cited

U.S. PATENT DOCUMENTS 5,066,575 11/1991 Sato et al. ........................ 430/558

OTHER PUBLICATIONS

CA 109(15):128599p Preparation of . . . fungicides. Buck et al., p. 648, 1988.

Primary Examiner—Mary C. Lee
Assistant Examiner—Joseph K. McKane
Attorney, Agent, or Firm—Arthur E. Kluegel

[57] ABSTRACT

A process is disclosed for the preparation of $^1$H-pyrazo [1,5-b][1,2,4]triazole magenta couplers represented by formula (I):

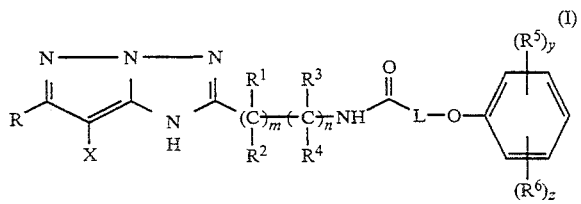

wherein R, $R^1$, $R^2$, $R^3$, $R^4$, $R^5$ each independently represents a hydrogen or a substituted or unsubstituted alkyl group, provided that $R^1$ and $R^2$ are not simultaneously a hydrogen atom; $R^6$ represents a substituted alkyl, aryl, alkoxy, aryloxy or other organic functional group; L represents a substituted or unsubstituted alkylene; m is an integer greater than zero; n, y, and z each represents an integer of zero to five; and X is a coupling off group.

The process comprises employing a nitrile compound of formula (II):

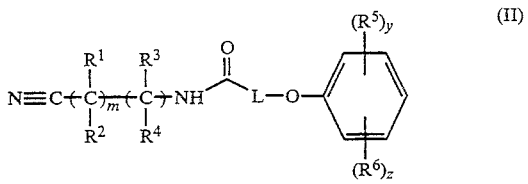

as an intermediate to obtain the compounds of formula (I).

9 Claims, No Drawings

INTERMEDIATES AND PROCESS FOR PREPARING MAGENTA COUPLERS

The present invention relates to a new process of preparing $^1$H-pyrazolo[1,5-b][1,2,4]triazole magenta couplers represented by formula (I):

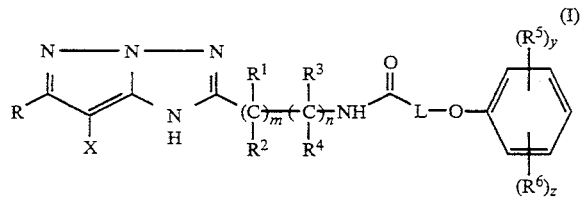

wherein R, $R^1$, $R^2$, $R^3$, $R^4$, $R^5$ each independently represents a hydrogen or a substituted or unsubstituted alkyl group, provided that $R^1$ and $R^2$ are not simultaneously a hydrogen atom; $R^6$ represents a substituted alkyl, aryl, alkoxy, aryloxy or other organic functional group; L represents a substituted or unsubstituted alkylene; m is an integer greater than zero; n, y, and z each represents an integer of zero to five; and X is a coupling off group; utilizing intermediate compounds of formula (II):

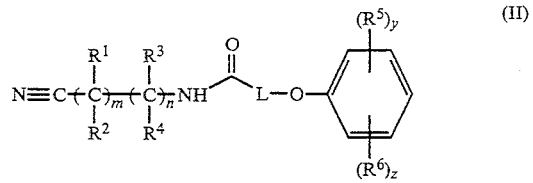

wherein R, $R^1$, $R^2$, $R^3$, $R^4$, $R^5$, $R^6$, m, n, y, z, X, and L are as defined above.

BACKGROUND OF INVENTION

Formula (I) includes pyrazolotriazole compounds which are useful as dye-forming $^1$H-pyrazolo[1,5-b][1,2,4]triazole couplers employed in color photographic silver halide materials, wherein R, $R^1$, $R^2$, $R^3$, $R^4$, $R^5$, $R^6$ and X are as defined above. Similar couplers are described in Japanese Kokai 2-201,443, which is equivalent to European Patent application 381,183 and U.S. Pat. No. 5,066,575 (hereafter referred to as "Sato"). For example, Sato discloses couplers of the formula:

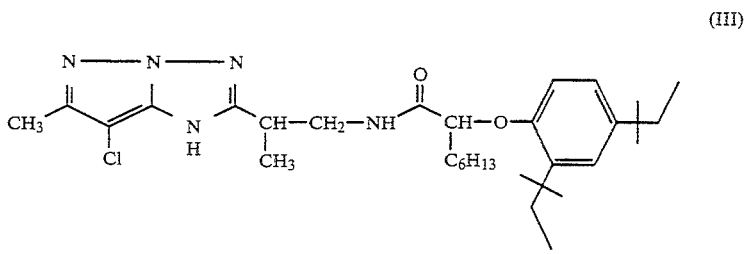

Sato further discloses a method of making such couplers. However, the disclosed process for preparing the couplers is complicated and entails considerable difficulties. Sato's scheme is as follows:

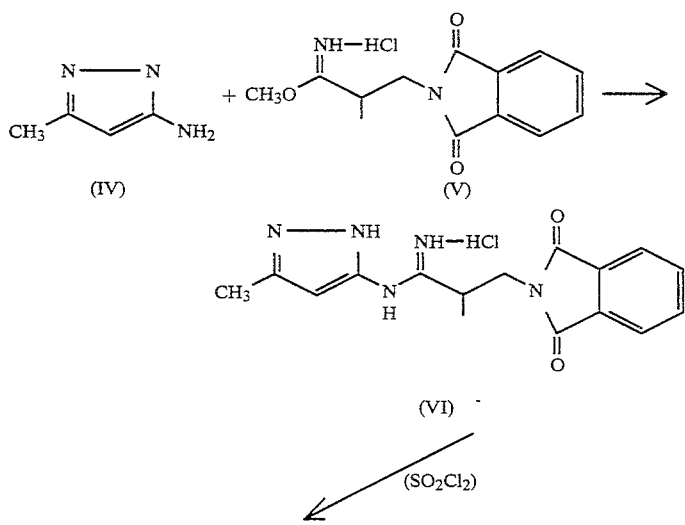

-continued

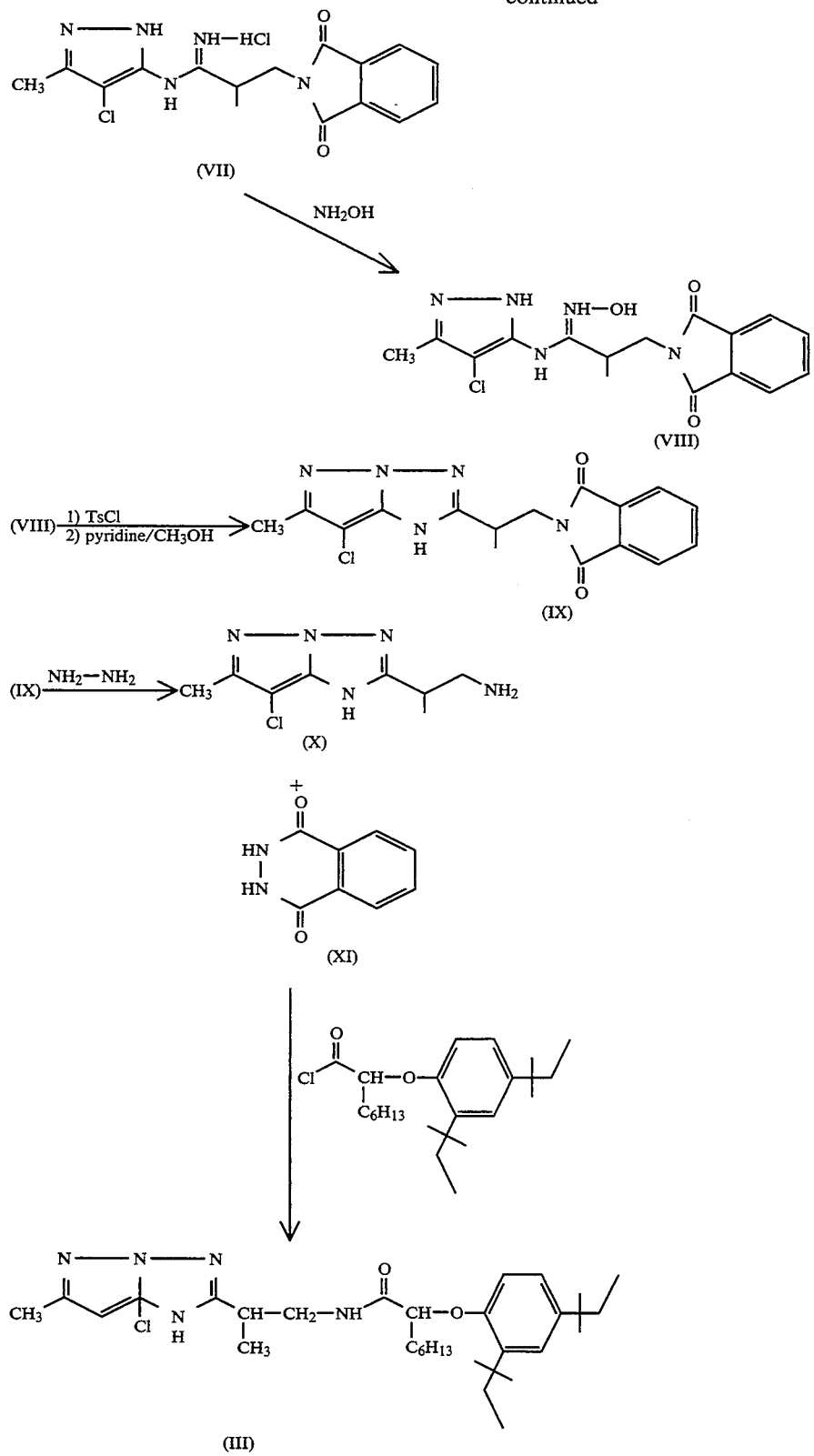

Sato's method is disadvantageous in that (1) the starting material (V) is not commercially available and its preparation requires a two-step process and (2) it is difficult to isolate the intermediate of formula (X) in a sufficiently pure form because this intermediate is always contaminated by a hydrazide of formula (XI), which is a by-product generated in the step of deblocking the intermediate of formula (IX). Consequently, the resulting amine of formula (X) is not sufficiently pure for the next step of the synthesis. Sato's process therefore requires a number of separation and purification steps.

SUMMARY OF THE INVENTION

In one embodiment, the present invention relates to intermediate compounds described by the following formula (II):

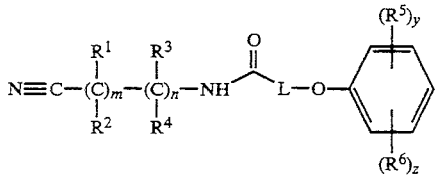

wherein R, $R^1$, $R^2$, $R^3$, $R^4$, $R^5$, $R^6$, m, n, y, z, X, and L are as defined above.

In another embodiment, the present invention relates to a process for the preparation of $^1$H-pyrazolo[1, 5-b][1,2,4]triazole magenta couplers of the above-described formula (I) from the intermediate compounds of formula (II). The process according to the present invention requires relatively fewer and simpler separation and purification steps.

DETAILED DESCRIPTION

The intermediate compound (II) of the present invention can be prepared according to the following general reaction scheme:

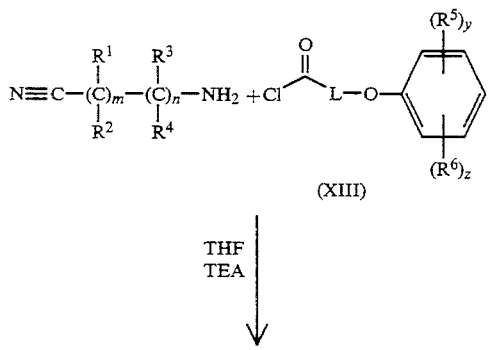

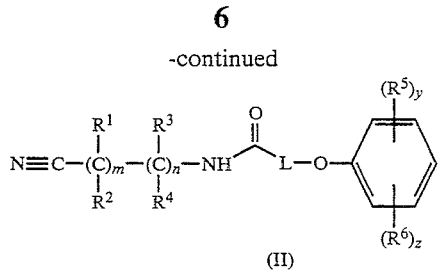

The above reaction is preferably conducted in an aprotic solvent such as tetrahydrofuran (THF), ethyl acetate, dioxane, pyridine, and dimethylformamide. A base is generally needed. Preferred bases include alkali metal salts of lower alcohols such as sodium methoxide, sodium ethoxide, sodium acetate, and potassium acetate. Organic bases can also be used such as triethylamine, pyridine, and 4-dimethylamino-pyridine. Preferred reaction temperatures are from about −10° C. to about 45° C. and preferred reaction time is from about 0.5 hours to about 18 hours.

The magenta couplers of formula (I) are prepared from compound (II) according to the following general reaction scheme:

1. The intermediate compound of formula (II) reacts with anhydrous hydrogen chloride and a lower alcohol of formula $R^7$-OH, wherein $R^7$ is lower alkyl, preferably methyl, ethyl, n-propyl, or isopropyl, to obtain a compound of formula (XIV):

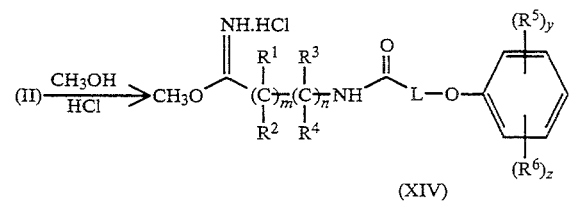

The reaction is preferably conducted in an acyclic or cyclic ether such as ethyl ether, n- or iso-propyl ether, dioxane, or tetrahydrofuran. The nature of the solvent is not critical and other solvents which are inert toward the reagents and products and which have the appropriate dissolving power for the starting materials and products to be dissolved can be used. The reaction preferably is carried out between about −30° C. to about 25° C. A preferred temperature range is −10° C. to 10° C. The above Pinner's reaction is described in greater detail in Sandler, S. R. and Karo, W., *Organic Functional Group Preparations*, vol. 3, ch. 8 (1989).

2. The preparation of the amidoxime of formula (XV) from the aminopyrazole of formula (XVII) is carried out in a two-step, one-pot process as follows:

(step 1)

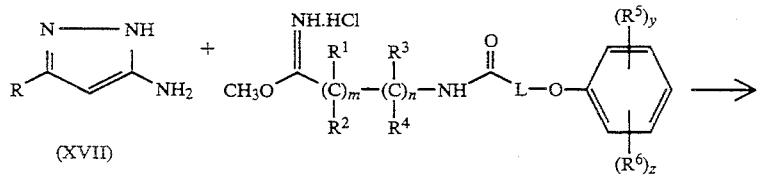

-continued

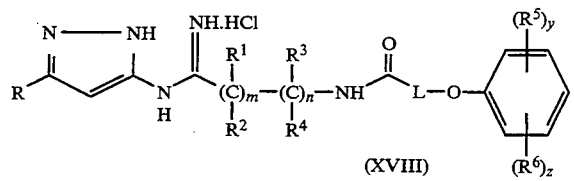

(XVIII)

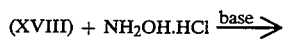

(step 2)

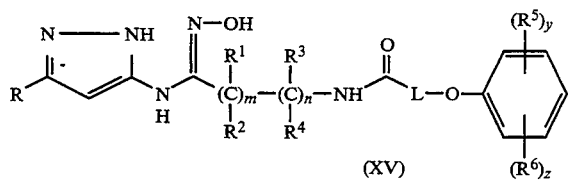

(XV)

The above reaction is preferably conducted in a solvent such as acetonitrile or a protic solvent such as methanol, ethanol or n- or iso-propanol. While these solvents are preferred, other solvents which are inert toward the reagents and products and which have the appropriate dissolving power for the starting materials and products to be dissolved can be used. Examples of other suitable solvents include ether, dioxane, or tetrahydrofuran. Mild reaction temperatures, such as between about $-5°$ C. and about $45°$ C. are preferred in ambient pressure with a reaction time of about 0.5 hrs. to about 10 hrs. The base utilized in the second step of the above reaction can be alkali metal salts of lower alcohols, particularly sodium methoxide, lithium methoxide, and sodium ethoxide.

3. The chlorination of the compound of formula (XV) yields the intermediate of formula (XVI). This reaction is preferably carried out in an aprotic solvent such as dichloromethane, N,N-dimethylformamide, chloroform, or tetrahydrofuran. Preferred chlorinating agents are N-chlorosuccinimide, 1,3-dichloro-5,5-dimethylhydantoin, and sulfuryl chloride. Preferred reaction temperatures are from about $-10°$ C. to about $45°$ C. The reaction scheme is illustrated as follows:

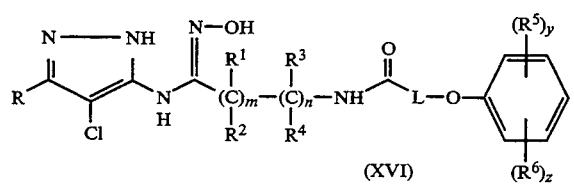

(XVI)

4. The pyrazolotriazole of formula (I) is obtained from the amidoxime of formula (XVI) by cyclization reaction. In a preferred embodiment, this is achieved via an intermediate of structure (XIX):

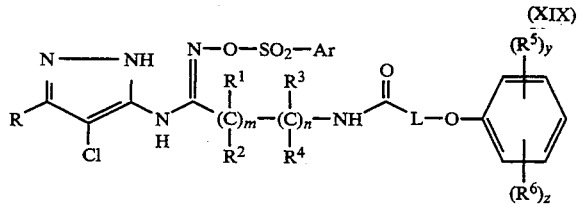

(XIX)

wherein Ar is a substituted aromatic ring.

For example, the intermediate (XIX) can be prepared by reacting the amidoxime of formula (XVI) with arylsulfonyl chloride in a suitable solvent, and this involves the activation of the oxime group towards the cyclization by attaching an efficient leaving group on the oxime functionality.

In this embodiment, the preparation of the intermediate of formula (XIX) is carried out in an aprotic solvent, such as THF, dioxane, ethyl acetate or methyl acetate, or other solvents which are inert with respect to the reactants and products. The reaction is conducted in the presence of a base. Preferred bases include aromatic amines such as substituted or unsubstituted pyridine and tertiary amines such as trialkylamines. The amount of the base may be 0.5 to 2 equivalents, and preferably, 1 equivalent. The preferred reaction temperature is between about $-5°$ C. and about $100°$ C., while the preferred reaction time is about 1 to about 10 hours.

The cyclization of the intermediate of formula (XIX) is preferably conducted in a protic solvent, such as a lower alcohol. The cyclization is carried out in the presence of a base. The nature and amount of the base is as previously defined for the preparation of the intermediate of formula (XIX). Preferred reaction temperature is between about $40°$ C. and about $100°$ C., while the preferred reaction time is from about 1 to about 15 hours.

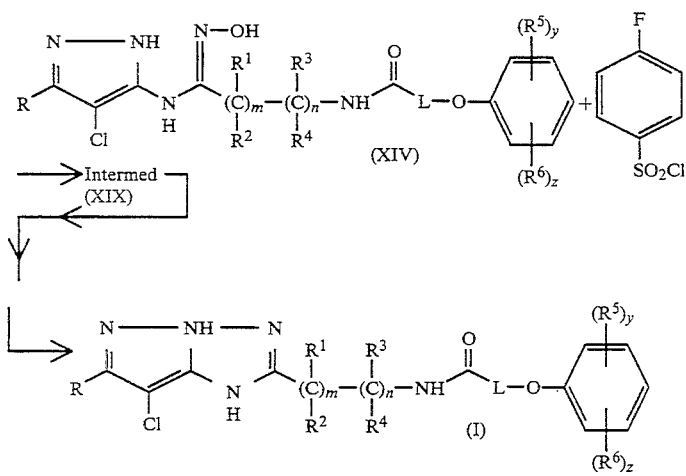

In the above formulas, R, $R^1$, $R^2$, $R^3$, $R^4$, $R^5$ each independently represents a hydrogen or a substituted or unsubstituted alkyl group, provided that $R^1$ and $R^2$ are not simultaneously a hydrogen atom. The term "alkyl" refers to branched and unbranched alkyl groups having 1 to 21 carbon atoms. These alkyl groups may be unsubstituted or substituted by one or more substituents. Preferred substituents are methyl, t-butyl, t-pentyl, pentadecyl, heneicosyl, and multicyclic rings connected through a fully substituted carbon.

$R^6$ represents a substituted or unsubstituted alkyl, aryl, alkoxy, aryloxy or an organic functional group having a carboxy group, a carbonamido group, a sulfonamido group, a sulfoxide group, a sulfone group, and an alkyl or arylamino group.

Examples of substituents for $R^6$ include an alkyl group which may be straight or branched and which may be substituted or unsubstituted, such as methyl, ethyl, n-propyl, n-butyl, t-butyl, trifluoromethyl, tridecyl or 3-(2,4-di-t-amylphenoxy)propyl; an alkoxy group which may be substituted, such as methoxy or ethoxy; an alkylthio group which may be substituted, such as methylthio or octylthio; an aryl group, an aryloxy group or an arylthio group, each of which may be substituted, such as phenyl, 4-t-butylphenyl, 2,4,6-trimethylphenyl, phenoxy, 2-methylphenoxy, phenylthio or 2-butoxy-5-t-octylphenylthio; a heterocyclic group, a heterocyclic oxy group or a heterocyclic thio group, each of which may be substituted and which contains a 3 to 7 membered heterocyclic ring composed of carbon atoms and at least one hetero atom selected from the group consisting of oxygen, nitrogen, and sulfur, such as 2-furyl, 2-thienyl, 2-benzimidazolyloxy or 2-benzothiazolyl; cyano; an acyloxy group which may be substituted, such as acetoxy or hexadecanoyloxy; a carbamoyloxy group which may be substituted, such as N-phenylcarbamoyloxy or N-ethylcarbamoyloxy; a silyloxy group which may be substituted, such as trimethylsilyloxy; a sulfonyloxy group which may be substituted, such as dodecylsulfonyloxy; an acylamino group which may be substituted, such as acetamido or benzamido; an anilino group which may be substituted, such as phenylanilino or 2-chloroanilino; an ureido group which may be substituted, such as phenylureido or methylureido; an imido group which may be substituted, such as N-succinimido or 3-benzylhydantoinyl; a sulfamoylamino group which may be substitute, such as N,N-dipropyl-sulfamoylamino or N-methyl-N-decyl-sulfamoylamino.

Additional examples of substituent groups include a carbamoylamino group which may be substituted, such as N-butylcarbamoylamino or N,N-dimethyl-carbamoylamino; an alkoxycarbonylamino group which may be substituted, such as methoxycarbonylamino or tetradecyloxycarbonylamino; an aryloxycarbonylamino group which may be substituted, such as phenoxycarbonylamino or 2,4-di-t-butylphenoxycarbonylamino; a sulfonamido group which may be substituted, such as methanesulfonamido or hexadecanesulfonamido; a carbamoyl group which may be substituted, such as N-ethylcarbamoyl or N,N-dibutylcarbamoyl; an acyl group which may be substituted, such as acetyl or (2,4-di-t-amylphenoxy) acetyl; a sulfamoyl group which may be substituted such as N-ethylsulfamoyl or N,N-dipropylsulfamoyl; a sulfonyl group which may be substituted, such as methanesulfonyl or octanesulfonyl; a sulfinyl group which may be substituted, such as octanesulfinyl or dodecylsulfinyl; an alkoxycarbonyl group which may be substituted, such as methoxycarbonyl or butyloxycarbonyl; an aryloxycarbonyl group which may be substituted, such as phenyloxycarbonyl or 3-pentadecyloxycarbonyl; an alkenyl group which may be substituted; a carboxyl group which may be substituted; a sulfo group which may be substituted; hydroxyl; an amino group which may be substituted; or a carbonamido group which may be substituted.

Substituents for the above substituted groups include halogen, an alkyl group, an aryl group, an aryloxy group, a heterocyclic or a heterocyclic oxy group, cyano, an alkoxy group, an acyloxy group, a carbamoyloxy group, a silyloxy group, a sulfonyloxy group, an acylamino group, anilino group, a ureido group, an imido group, a sulfonylamino group, a carbamoylamino group, an alkylthio group, an arylthio group, a heterocyclic thio group, an alkoxycarbonylamino group, an aryloxycarbonylamino group, a sulfonamido group, a carbamoyl group, an acyl group, a sulfamoyl group, a sulfonyl group, a sulfinyl group, an alkoxycarbonyl group, an aryloxycarbonyl group, an alkenyl group, a carboxyl group, a sulfo group, hydroxyl, an amino group or a carbonamido group.

L represents a linking group. Suitable L groups include

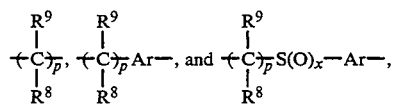

wherein
p is an integer of 1 to 6, x is 0, 1 or 2, $R^8$ and $R^9$ independently represent a hydrogen atom or a substituent; and Ar represents a substituted or unsubstituted phenyl group.

m is an integer greater than zero, preferably 1 to 6.

n, y, and z each represents an integer of zero to five.

"Coupling off group", as used herein, are those coupling off groups known in the art. Such groups can determine the equivalency of the coupler, or can advantageously affect the layer in which the coupler is coated or other layers in the element by performing, after release from the coupler, such functions as development inhibition, development acceleration, bleach inhibition, bleach acceleration, color correction, and the like. Representative classes of coupling off groups include halogen, particularly chlorine, bromine, or fluorine, alkoxy, aryloxy, heterocyclyloxy, heterocyclic, such as hydantoin and pyrazolo groups, sulfonyloxy, acyloxy, carbonamido, imido, acyl, heterocyclylimido, thiocyano, alkylthio, arylthio, heterocyclylthio, sulfonamido, phosphonyloxy and arylazo. They are described in, for example, U.S. Pat. Nos. 2,355,169; 3,227,551; 3,432,521; 3,476,563; 3,617,291; 3,880,661; 4,052,212, and 4,134,766; and in U.K. Patents and published application numbers 1,466,728; 1,531,927; 1,533,039; 2,006,755A and 2,017,704A; the disclosures of which are incorporated herein by reference.

Examples of specific coupling off groups are Cl, F, Br, —SCN, —OCH$_3$, —OC$_6$H$_5$, —OCH$_2$C(=O)NHCH$_2$CH$_2$OH, —OCH$_2$C(=O)NHCH$_2$CH$_2$OCH$_3$, —OCH$_2$C(=O)NHCH$_2$CH$_2$OC(=O)OCH$_3$, —NHSO$_2$CH$_3$, —OC(=O)C$_6$H$_5$, —NHC(=O)C$_6$H$_5$, —OSO$_2$CH$_3$, —P(=O)(OC$_2$H$_5$)$_2$, —S(CH$_2$)$_2$CO$_2$H,

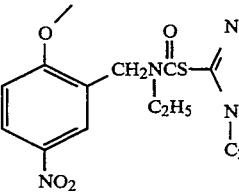

Preferably, the coupling off group is H or halogen, and more preferably, H or Cl.

Some examples of $^1$H-pyrazo[1, 5-b][1,2,4]triazole couplers of formula (I) which can be prepared according to the present invention are:

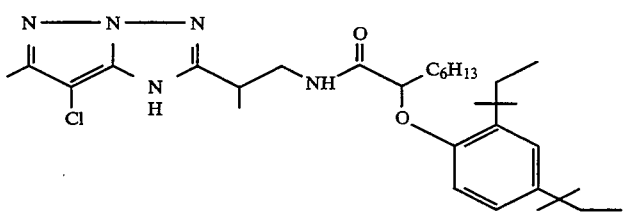

M-1

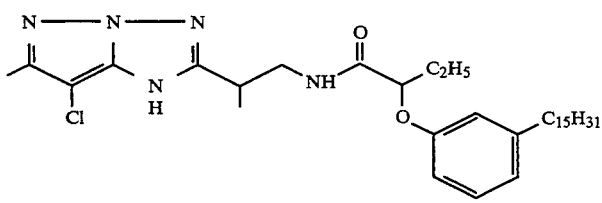

M-2

-continued
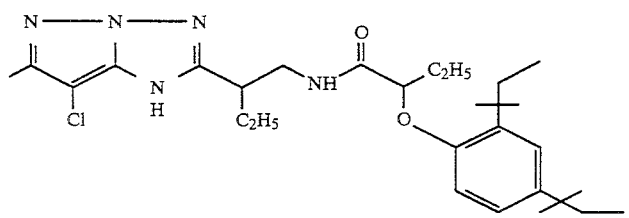
M-3
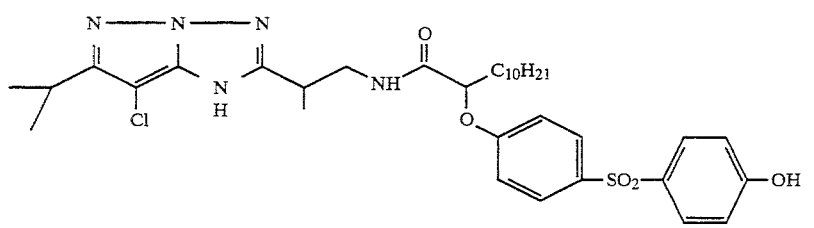
M-4
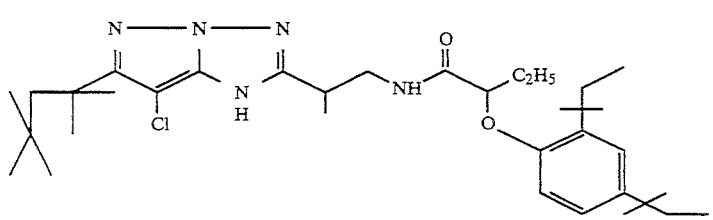
M-5
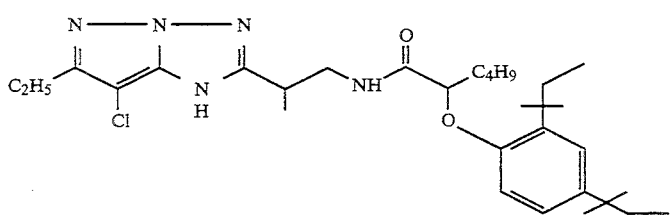
M-6
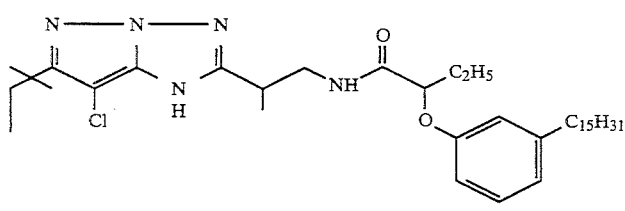
M-7
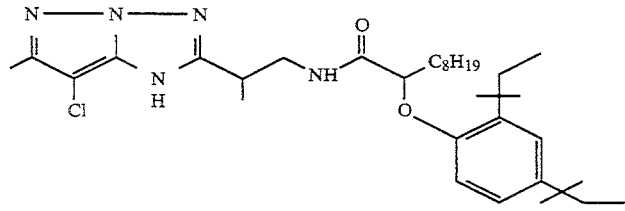
M-8
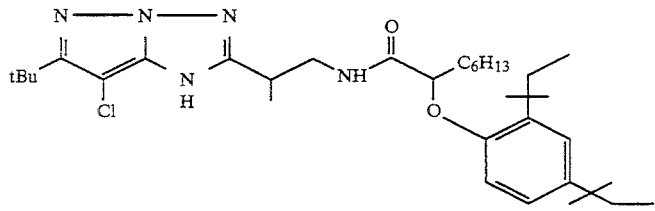
M-9

-continued
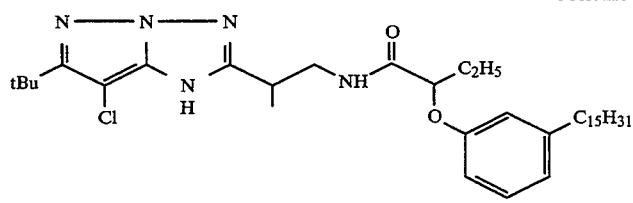 M-10
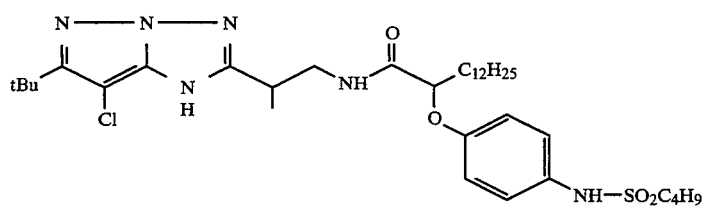 M-11
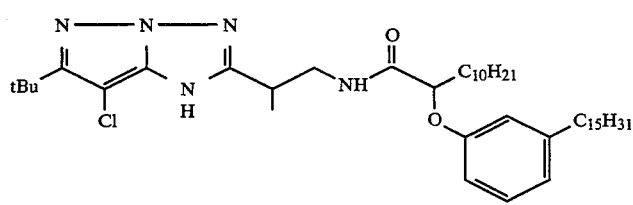 M-12
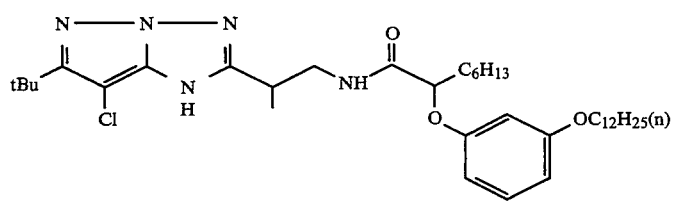 M-13
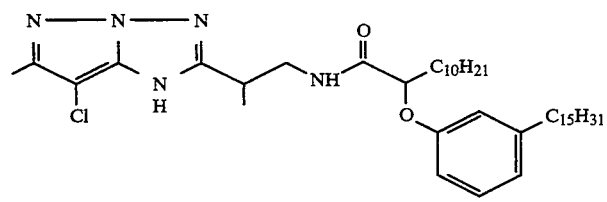 M-14
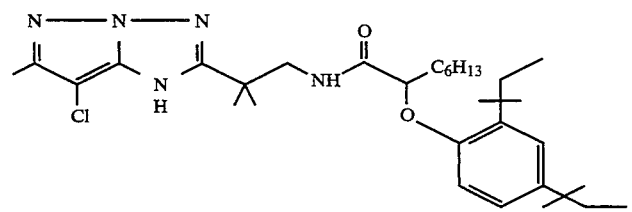 M-15
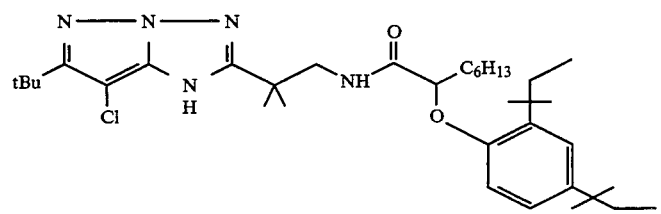 M-16
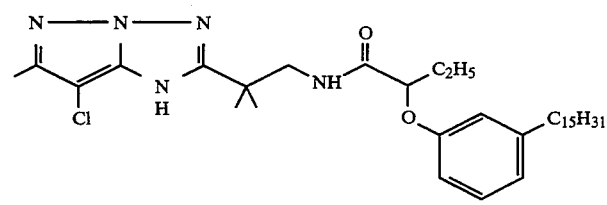 M-17

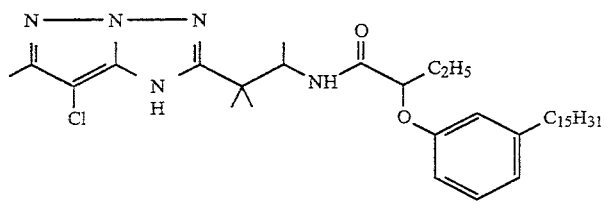
M-18
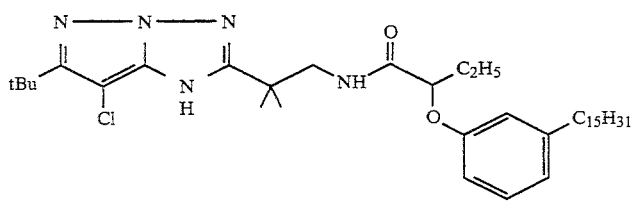
M-19
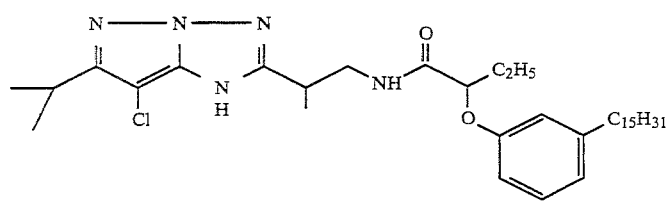
M-20
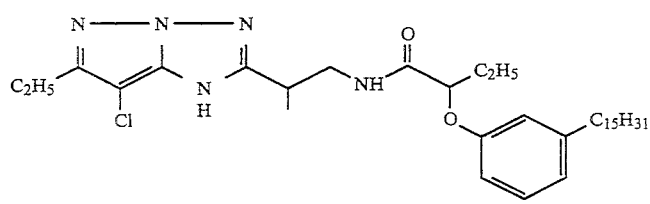
M-21
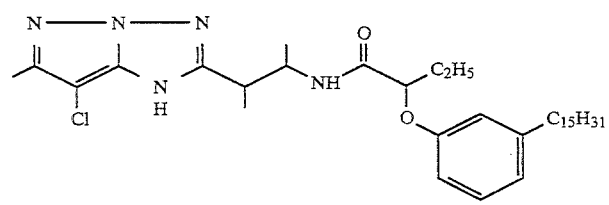
M-22
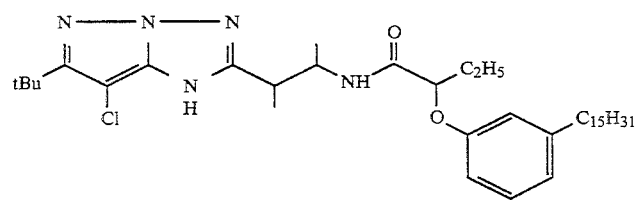
M-23
The present invention is further illustrated by, though in no way limited to, the following examples.
REACTION SCHEME FOR M-1
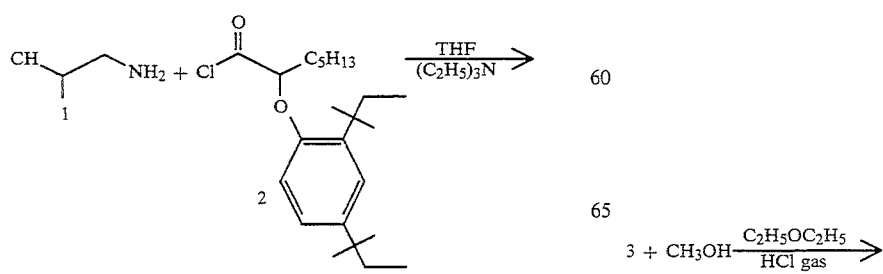
-continued
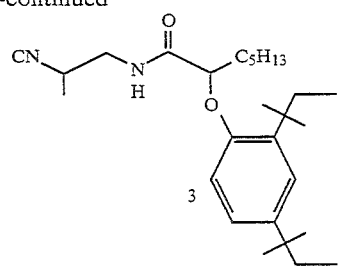
$3 + CH_3OH \xrightarrow[\text{HCl gas}]{C_2H_5OC_2H_5}$ -continued

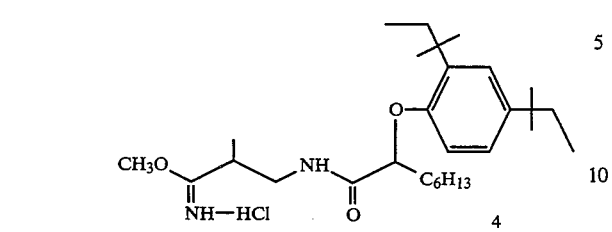

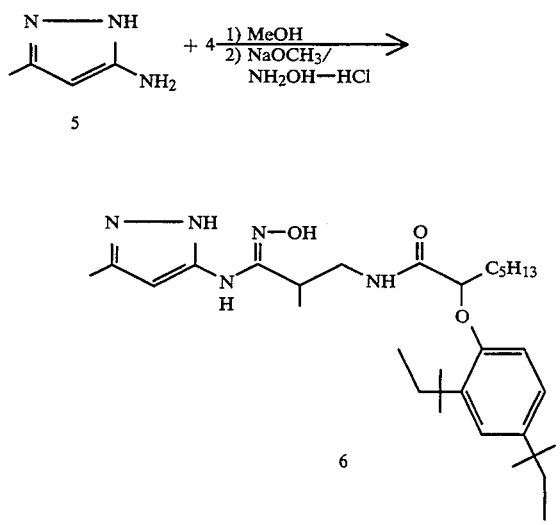

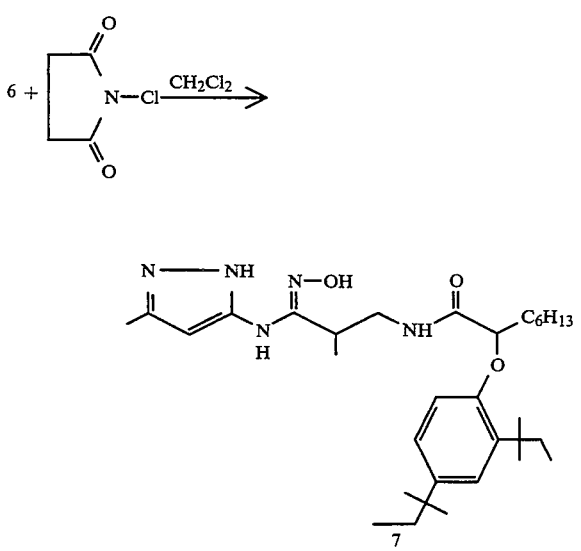

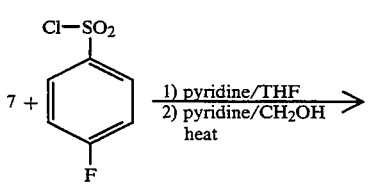

-continued

M-1

Preparation of Compound 3

Compound 3 in the above scheme was prepared as follows. A solution of 16.80 g (0.20 mol) of 2-cyanopropylamine (1) dissolved in 160 ml of THF was cooled to 0° C. This was followed by the one-portion addition of 21.25 g (0.21 mol) of triethylamine and the drop-wise addition of 82 g (0.208 mol) of 2-(2,4-bis(1,1-dimethylpropyl)phenoxy)octanoyl chloride in 300 ml of THF. After the addition was completed, the reaction mixture was stirred for 2 hours. At that time, no starting material remained as evidenced by thin layer chromatography analysis of the reaction mixture. (elution: Ligroin/$CH_2Cl_2$/AcOEt: 4/2/1). The reaction mixture was poured into a mixture of ice water, acidified to a pH value in the 1–2 range. The organic product was extracted with ethyl acetate. The combined extracts were washed with two 200-ml portions of a 10% solutions of $Na_2CO_3$, one 200-ml portion of water and one 200-ml portion of a 10% solution of HCl. The organic layer was dried over $MgSO_4$ and filtered. The filtrate was concentrated in vacuo to yield the crude product which was purified by column chromatography (elution: Ligroin/$CH_2Cl_2$/AcOEt: 80/15/5). The yield of the purified product was 57.54 g (65%). All analytical data confirmed the assigned structure.

Synthesis of Compound (4)

Compound 4 in the above scheme was prepared as follows. A solution of 180 g (0.406 mol) of compound (3) dissolved in 1440 ml of anhydrous ether was cooled to −10° C., followed by the saturation of hydrogen chloride gas. During the bubbling of the gas, the solution temperature was maintained at −10° C. 14.4 g (0.45 mol) of methanol was added to the reaction mixture. After the mixture had been stirred for 5 minutes, the flask was sealed and placed in a freezer for 48 h. The flask and the reaction mixture were allowed to warm up to room temperature. The solution was concentrated in vacuo to yield a white solid: 207.5 g (100%). Proton NMR confirmed the assigned structure.

Preparation of Compound (6)

Compound 6 of the above scheme was prepared as follows. A suspension of 20.39 g (0.22 mol) of 5-amino-3-methyl pyrazole (5) and 107.30 g (0.21 mol) of compound (4) in 1.30 liter of anhydrous methanol was heated with vigorous stirring for 8 h. At that time, the reaction was complete, as evidenced by the thin layer chromatography analysis ($CH_2Cl_2$/AcOEt/$CH_3OH$: 2/2/1). The reaction was allowed to cool to room temperature, followed by the one-portion addition of 15.29 g (0.22 mol) of hydroxylamine hydrochloride. The reaction was stirred for 10 minutes, followed by the portion-wise addition of 450 ml of a 0.5 mol/1 solution of sodium methoxide in methanol. The reaction mixture was heated at 45°–50° C. for 18 h. At that time, the reaction was complete, as evidenced by the TLC. The reaction mixture was poured into a mixture of ice-water. The organic product was extracted with two 600-ml portions of ethyl acetate. The organic layer was dried over MgSO4 and filtered. The filtrate was concentrated in vacuo to yield an oil: 96.78 g (80%). Proton NMR confirmed the assigned structure. The recovered compound 6 was used in the next step without further purification.

Preparation of Compound (7)

Compound 7 in the above scheme was prepared as follows. 40.0 g (0.30 mol) of N-chlorosuccinimide (NCS) was added in one portion to a solution of 166.70 g (0.30 mol) of compound (6) dissolved in 1.7 liter of methylene chloride at room temperature. The reaction mixture was stirred overnight. The mixture was concentrated in vacuo to yield a residue. The residue was dissolved in 500 ml of AcOEt and the solution was washed with three 100-ml portions of a 10% solution of aqueous hydrochloric acid and with water. The organic layer was dried over MgSO4 and filtered. The filtrate was concentrated in vacuo to yield a light brown oil: 168.25 g (95%). Proton NMR confirmed the assigned structure. The recovered compound 7 was used in the next step.

Synthesis of Coupler (M-1)

Coupler M-1 was prepared as follows. A solution of 147.55 g 90.25 mol of compound (7) dissolved in 1.4 liter of tetrahydrofuran was cooled to 0° C. followed by the addition of 20.56 g (0.26 mol) of pyridine. The mixture was stirred for 5 minutes and 50.5 g (0.26 mol) of para-fluorobenzenesulfonyl chloride was added over a period of 30 minutes. During the addition, the reaction temperature was maintained at 0°–5° C. The reaction was stirred at that temperature for one hour and was allowed to warm up to room temperature. At that time, the reaction was complete, as evidenced by the TLC analysis (elution: CH2Cl2/AcOEt: 3/1). The reaction mixture was concentrated in vacuo. To the resulting oil were added 1.4 liter of methanol and 20.56 g (0.26 mol) of pyridine. The mixture was heated at reflux for 1 h. The thin layer chromatography (CH2Cl2/AcOEt: 3/1) indicated the completion of the reaction. The mixture was cooled to room temperature and poured into a mixture of ice-water containing 0.52 moles of concentrated HCl acid. The organic product was extracted with two 600-ml portions of AcOEt. The combined extracts were washed with three 150-ml portions of a 10% solution of NaHCO3 and with brine. The organic layer was dried over MgSO4 and filtered. The filtrate was concentrated in vacuo to yield a heavy oil which was purified by flash column chromatography. The yield at that point was 135.90 g (95%). All the analytical data confirmed the assigned structure of M-1. The material was further purified by recrystallization from octane to yield a white solid 71.53 g (50%).

While the invention has been described in detail and with reference to specific embodiments thereof, it will be apparent to one skilled in the art that various changes and modifications can be made therein without departing from the spirit and scope of the invention.

What is claimed is:

1. A compound of formula (II):

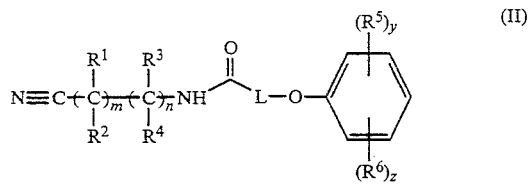

wherein $R^1$, $R^2$, $R^3$, $R^4$, and $R^5$ each independently represents a hydrogen or a substituted or unsubstituted alkyl group, provided that $R^1$ and $R^2$ are not simultaneously a hydrogen atom; $R^6$, which is substituted or unsubstituted, is selected from the group consisting of sulfonamido and arylamino; L represents a substituted or unsubstituted alkylene; m is an integer greater than zero; y represents an integer of zero to five; and n and z each represents an integer of 1 to 5.

2. The compound of claim 1 wherein L is selected from the group consisting of

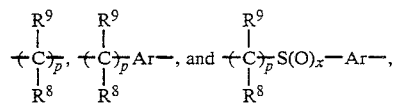

wherein p is an integer of 1 to 6, x is 0, 1 or 2, $R^8$ and $R^9$ independently represent a hydrogen atom or an alkyl group; and Ar represents a substituted or unsubstituted phenyl group.

3. The compound of claim 1 wherein m is an integer of 1 to 6.

4. The compound of claim 1 wherein at least one of $R^1$, $R^2$, $R^3$, $R^4$, and $R^5$ is substituted with one or more substituent(s).

5. The compound of claim 3 wherein the substituent(s) are selected from the group consisting of methyl, t-butyl, t-pentyl, pentadecyl and heneicosyl.

6. The compound of claim 1 wherein $R^6$ is substituted with one or more substituent(s) selected from the group consisting of alkyl, alkoxy, alkylthio, aryl, aryloxy, and arylthio.

7. The compound of claim 1 wherein L is —CH(C2H5)—.

8. The compound of claim 1 wherein L is —CH(C6H13)—.

9. The compound of claim 1 wherein n represents an integer of 2 to 5.

* * * * *

IN THE UNITED STATES PATENT AND TRADEMARK OFFICE
CERTIFICATE OF CORRECTION

PATENT NO.   : 5,395,968
DATED        : March 7, 1995
INVENTOR(S)  : Ping W. Tang, et al.

It is certified that an error appears in the above-identified patent and that said Letters Patent is hereby corrected as shown below:

Cover [75] Inventor: Ping-Wah Tang, insert --Terry Mungal, both of--.

Signed and Sealed this

Twenty-sixth Day of September, 1995

Attest:

BRUCE LEHMAN

*Attesting Officer*        *Commissioner of Patents and Trademarks*